United States Patent [19]

Rydell

[11] Patent Number: 5,342,359
[45] Date of Patent: Aug. 30, 1994

[54] BIPOLAR COAGULATION DEVICE

[75] Inventor: Mark A. Rydell, Golden Valley, Minn.

[73] Assignee: Everest Medical Corporation, Minneapolis, Minn.

[21] Appl. No.: 13,832

[22] Filed: Feb. 5, 1993

[51] Int. Cl.$^5$ ............................................. A61B 17/39
[52] U.S. Cl. .................................................... 606/51
[58] Field of Search ..................... 606/46, 48, 50, 51, 606/52

[56] References Cited

U.S. PATENT DOCUMENTS

| | | |
|---|---|---|
| 1,814,791 | 7/1931 | Ende . |
| 3,920,021 | 11/1975 | Hiltebrandt . |
| 4,003,380 | 1/1977 | Wien . |
| 4,005,714 | 2/1977 | Hiltebrandt . |
| 4,041,952 | 8/1977 | Morrison, Jr. et al. . |
| 4,311,145 | 1/1982 | Esty et al. . |
| 4,418,692 | 12/1983 | Guay . |
| 4,461,305 | 7/1984 | Cibley . |
| 4,657,016 | 4/1987 | Garito et al. . |
| 4,938,761 | 7/1990 | Enselin . |
| 5,009,661 | 4/1991 | Michelson . |
| 5,026,370 | 1/1991 | Lottick . |
| 5,078,717 | 1/1992 | Parins et al. . |
| 5,217,460 | 6/1993 | Knoepfler ......................... 606/52 |
| 5,258,006 | 11/1993 | Rydell et al. ...................... 606/32 |
| 5,269,780 | 12/1993 | Roos ................................. 606/50 |

FOREIGN PATENT DOCUMENTS

| | | |
|---|---|---|
| 2808911 | 3/1979 | Fed. Rep. of Germany . |
| 3709067 | 9/1988 | Fed. Rep. of Germany . |
| 649420 | 3/1979 | U.S.S.R. . |

OTHER PUBLICATIONS

U.S. Statutory Invention Reg. No. H1028 Falk et al., Mar. 3, 1992.
"Two New Laparoscopic Instruments: Bipolar Sterilizing Forceps and Uterine Manipulator" by Stephen Corson, Medical Instrumentation, vol. 11, No. 1.
Cameron–Miller product brochure for Model 80-7527.

*Primary Examiner*—Lee S. Cohen
*Attorney, Agent, or Firm*—Haugen and Nikolai

[57] ABSTRACT

A bipolar coagulation instrument comprising three concentric tubes, wherein the outer tube is generally rigid, the central tube is an electrically conductive metal in communication with an energy source, and the inner tube is electrically non-conductive. The distal end of the central tube extends beyond the distal end of the outer tube and functions as an electrode and first jaw of the coagulation instrument. The inner tube, which is translationally movable by an operator, has extending therethrough within its lumen a conductive lead whose distal end protrudes distally therefrom beyond the distal end of the outer tube and is configured at its distal end to function as an opposing second jaw to the first jaw. Translational movement of the inner tube distally forces the second electrode jaw toward the first electrode jaw to thereby bring the first and second jaws into contact with each other. Thereafter, when current is introduced to the conductive lead and to the central tube, the resulting electrode jaws perform to cauterize tissue at the treatment site when such tissue is grasped within the jaws which are then closed. Subsequent proximal translational movement of the inner tube releases the distal end of the conductive lead which is the second jaw of the instrument from the distal end of the central tube which is the first jaw of the instrument. A coagulation instrument is thereby provided whose outer tube has a diameter of less than about three millimeters, thereby permitting its travel within the lumen of a minimally sized laparoscope, endoscope or similar device.

7 Claims, 2 Drawing Sheets

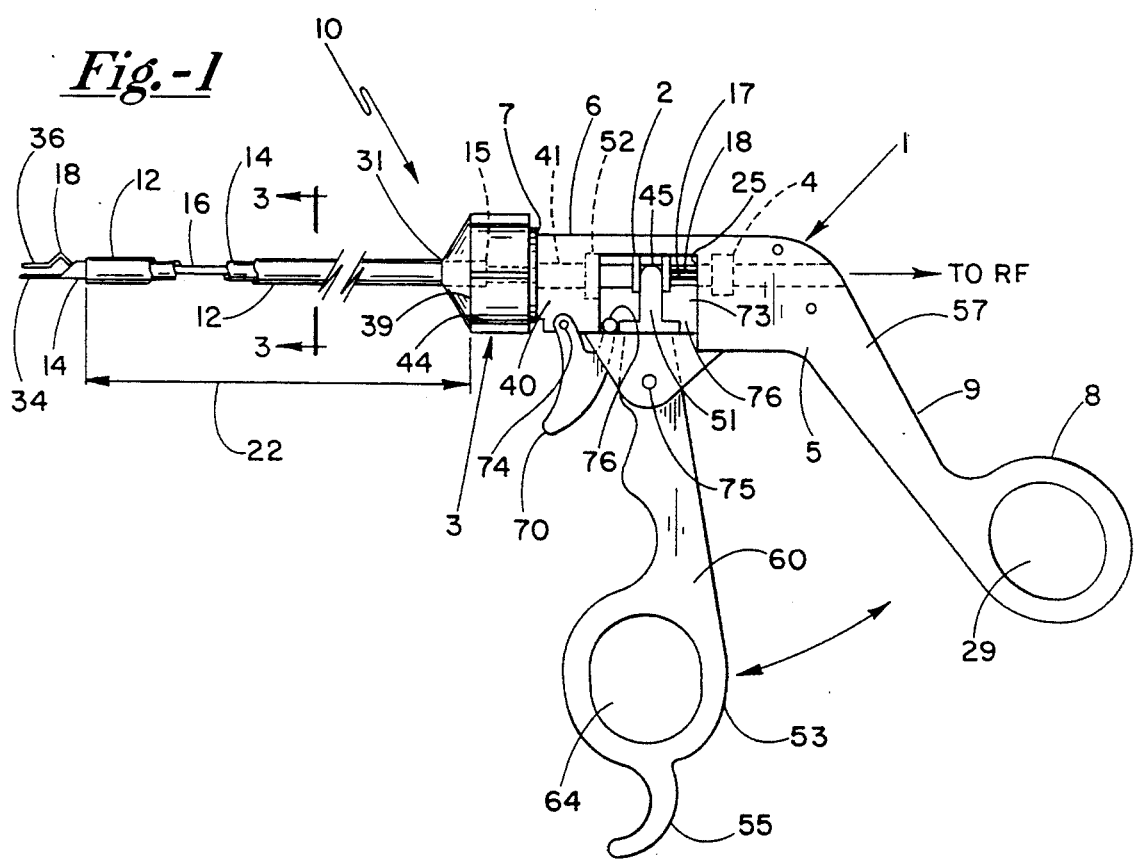
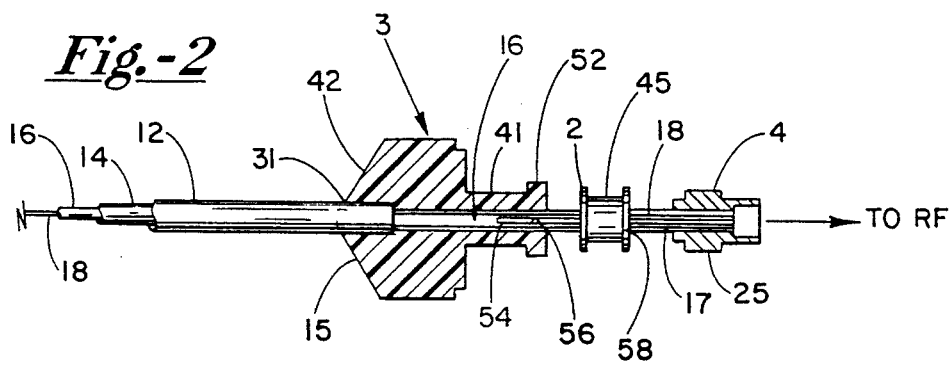
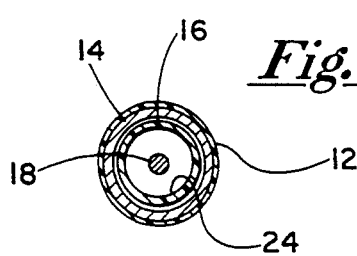

BIPOLAR COAGULATION DEVICE

BACKGROUND OF THE INVENTION

I. Field of the Invention

This invention relates generally to electrosurgical instruments, and more particularly to a bipolar electrosurgical coagulation instrument specifically designed for use in the performance of laparoscopic, endoscopic or similar procedures.

II. Discussion of the Prior Art

Heat has been used for the cauterization of bleeding wounds for centuries. Recently, the use of radio frequency (RF) energy traveling through the body has been widely used to stop bleeding. The RF energy cauterizes the blood vessels by heating proteins in the blood to a temperature where the proteins congeal. RF energy is preferred because its frequency is above that which could otherwise cause neuromuscular stimulation. At least two modes of RF cauterization are typically employed, namely monopolar or bipolar coagulation.

A monopolar electrosurgical system usually consists of an RF generator unit, an active electrode of small dimensions, and a large area return or dispersive electrode designed to be placed on the patients buttocks or thigh to serve as a return point for the RF energy released at the active electrode site. The active electrode is applied to the bleeding site and the current path is completed through the body to the return electrode which is electrically in contact with the patients skin surface.

Bipolar electrosurgical devices have the inherent advantage over monopolar devices of containing the RF energy. In a bipolar device, both the active and the return electrodes are placed on the surgical instrument. Thus, no separate return electrode on the patient is required as in monopolar systems. The RF energy remains at the site where the device is being used and only effects patient tissue in close proximity. Generally, bipolar devices are able to achieve the same results as competing monopolar devices while using a lower level of RF energy. Potential patient complications related to monopolar RF energy traveling through the body on a somewhat unpredictable path to the return electrode are avoided.

In the past, to cauterize blood vessels during a laparoscopic, endoscopic or similar procedure, either a cutting laser was used for small bleeding blood vessels, or a monopolar cauterization instrument was used for larger bleeders. These methods, however, have two significant drawbacks. Monopolar instruments, using RF energy, often have an unpredictable current flow path back to the return electrode. This unpredictable current flow may have a destructive effect on surrounding tissues. While non-contact positioning of a laser may overcome this problem, the laser has no way of holding a bleeding vessel and is not used on larger bleeders. The present invention overcomes both of these drawbacks by utilizing bipolar energy applied in an instrument that can effectively cauterize a bleeding blood vessel or vessels.

U.S. Pat. No. 4,005,714, entitled "Bipolar Coagulation Forceps," describes a forceps device which has two insulated current conductors terminating in a coaxial plug and a coaxial contact bushing. The conductors may be opened and closed by shifting an outer actuating sleeve with the aid of a handle that is stationary in relation to the forceps arms. The device moves the outer sleeve translationally in relation to the inner stationary sleeve and forceps device. In contrast, in the present invention an inner tube moves translationally within two concentric stationary outer tubes. The device of the '714 patent also differs from the present invention in that it has no means built into the handle for permitting rotation of the distal end of the instrument without turning the entire device. Conversely, the invention described herein incorporates the flexibility of a rotating distal end combined with a stationary handle to thereby better facilitate treatment of bleeding vessels. The present invention also allows introduction of a preset gap between opposing electrode surfaces to preclude shorting of the leads at the distal end and give better control over cauterization of bleeding tissue.

U.S. Pat. No. 3,920,021, describes devices for coagulating animal tissue by means of high frequency current. The device, as depicted, appears to show bipolar electrodes at the distal end of an outer tube. The proximal end of the outer tube and the proximal end of the inner tube are attached to a squeezable device that will move both the outer tube and the inner tube. Hence, neither the outer tube nor the inner tube is translationally stationary in relation to the handle. The device described in the '021 patent does not contain a means for rotating its distal end while holding the handle stationary or means for introducing a preset gap between the forceps' jaws.

Co-pending and commonly assigned U.S. patent application Ser. No. 08/013,852, filed Feb. 5, 1993, and entitled "Bipolar Electrosurgical Forceps," discloses a bipolar forceps device wherein both blades of the forceps move in relation to each other between an open and a closed configuration. This dual blade movement, while highly efficient, results in a device whose cross-sectional dimension may be too large for use in certain laparoscopic, endoscopic or similar procedures since the device is too large for travel within the lumen of such instrumentation.

The present invention is directed to a bipolar electrosurgical coagulation instrument which is specifically designed to be insertable through a canula for use in coagulating and cauterizing during laparoscopic, endoscopic or similar surgical procedures.

It is accordingly a primary object of the present invention to provide an electrosurgical instrument for carrying out laparoscopic, endoscopic or similar cauterization procedures.

Another object of the present invention is to provide an improved electrosurgical cauterization instrument for performing cauterization procedures requiring instrumentation travel through a scope canula of minimal cross-section dimension.

Yet another object of the present invention is to provide a bipolar electrosurgical instrument allowing better control over the location of cauterization treatment.

Yet another object of the present invention is to provide a bipolar electrosurgical cauterization instrument that has a rotatable distal end at the site of a procedure.

These and other objects of the present invention will become apparent throughout the following description.

SUMMARY OF THE INVENTION

The foregoing features and advantages of the present invention are attained by providing a bipolar electrosurgical coagulation instrument comprising, first of all, three concentric tubes. The outer tube is generally rigid, the central tube is an electrically conductive metal in communication with an electrical connector, and the inner tube is electrically nonconductive. The distal end of the central tube extends beyond the distal end of the outer tube and functions as an electrode and first jaw of the present coagulation device. The inner tube, which is translationally movable by an operator, has extending therethrough within its lumen a conductive lead whose distal end protrudes distally therefrom beyond the distal end of the outer tube. The distal end of the lead is configured to provide three shaped zones. The first, more proximal zone, is angled upwardly from the immediately proximal longitudinal axis of the lead to thereby form an upward ramp. The second zone is angled downwardly, while the third zone is angled forwardly to be substantially parallel with the axis of the lead proximal to the first zone and to thereby function as an opposing second jaw to the first jaw. Translational movement of the inner tube distally forces the second electrode jaw toward the first electrode jaw as a proximal portion of the upward ramp of the lead enters the inner tube to thereby bring the first and second jaws into contact with each other. As is evident, when current is introduced to the leads, the electrode jaws perform to cauterize tissue at the treatment site when such tissue is grasped within the jaws which are then closed. Subsequent proximal translational movement of the inner tube releases the upward ramp from the inner tube and the second jaw parts from the first jaw. Employment of the above described construction can provide a coagulation instrument whose outer tube has a diameter of less than about three millimeters, thereby permitting its travel within the lumen of a minimally sized laparoscope, endoscope or similar device.

The coagulation instrument of the present invention further has a handle member that contains a means for simultaneously rotating the inner, central and outer tubes as well as the electrode jaws while maintaining the handle stationary. The handle further contains a means for translationally moving the inner tube to effectuate jaw closing and opening as described above. In the preferred embodiment of the device, the means for rotation is a knob located at the proximal end of the tubes and the distal end of the handle. The knob is of a first diameter but has an inner extension which cooperates with the tubes and leads to provide rotatability. Translational movement of the inner tube is accomplished by connecting the inner tube to an arm that is pivotally attached to the main body of the handle. When the pivotally attached arm is moved in a scissors like manner, the inner tube is made to move reciprocally within the lumen of the central tube.

To preclude shorting of the electrode jaws and to give better control over coagulation of bleeding tissue, the handle member contains a finger activated safety catch or trigger. The trigger, when activated, prevents the handle member from effectuating further translational motion of the inner tube and precludes the complete closing of the electrode jaws.

BRIEF DESCRIPTION OF THE DRAWINGS

FIG. 1 is a side elevation view, partially cut away, of a bipolar coagulation instrument;

FIG. 2 is a side elevation view, partially in section, of the central portion of the instrument of FIG. 1;

FIG. 3 is a cross-section along line 3—3 of FIG. 1;

DESCRIPTION OF THE PREFERRED EMBODIMENT

Figure 4A:
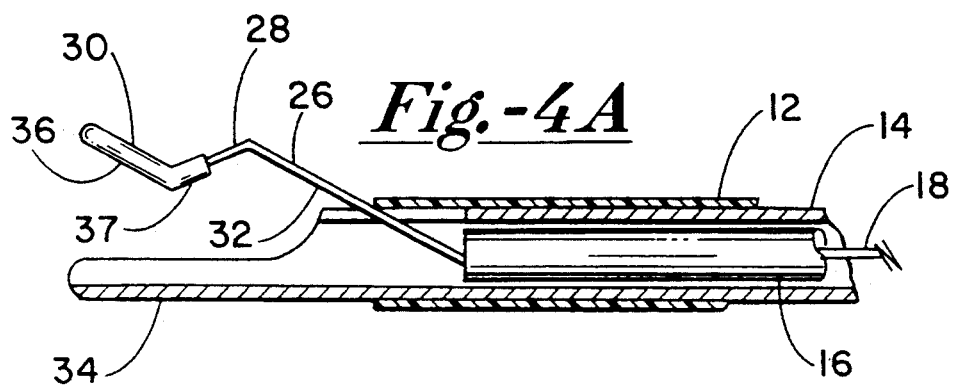
FIG. 4a is an enlarged side elevation view, partially in section of the distal portion of the instrument of FIG. 1 in an open position.
Figure 4B:
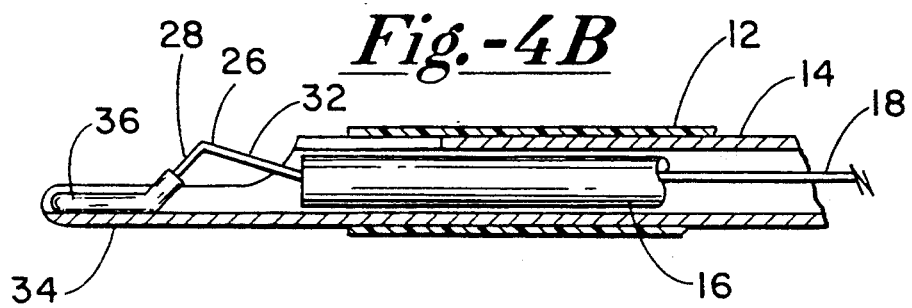
FIG. 4b is an enlarged side elevation view as in FIG. 4a, except in a closed position.
Figure 5:
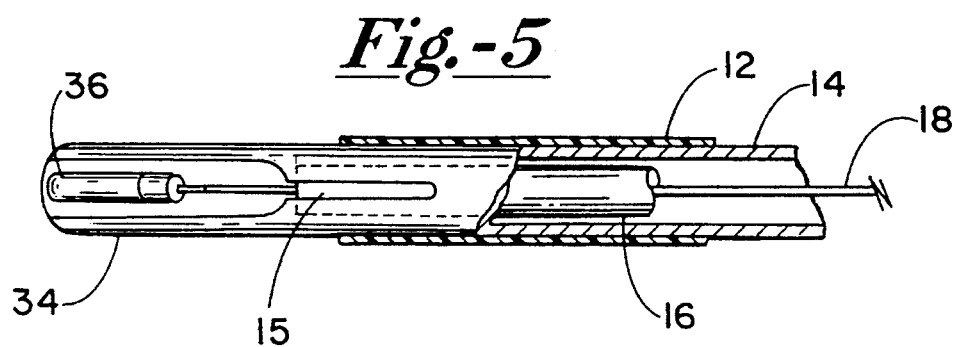
FIG. 5 is a top plan view, partially in section, of the distal portion of the instrument of FIG. 1.

Referring to FIGS. 1–6, an electrosurgical coagulation instrument 10 is illustrated. The instrument 10 generally comprises an elongated, rigid outer tube 12, an electrically conductive central tube 14, an electrically insulated inner tube 16, a conductive lead 18 within the inner tube 16, and a scissors-style handle member 1. The handle member 1 is made from a medical grade plastic, such as a 20% glass filled polycarbonate material; the inner tube 16 is made from nylon, and the central tube 14 is metal. The outside diameter of the inner tube 16 is small enough to fit loosely inside the lumen of the central tube 14. This allows the inner tube 16 to translationally slide inside the central tube 14. The outside diameter of the outer tube 12 is small enough to pass through a canula of about three millimeters diameter, and the length 22 is sufficient to reach an internal blood vessel to be cauterized when a canula/scope procedure is performed.

The distal end of the central tube 14 extends distally beyond the distal end of the outer tube 12. The top half of the most distal portion of the distal end of the central tube 14 is absent, and the remaining floor thereof is flattened to thereby form a first electrode jaw 34 of the coagulation instrument 10. The distal end of the inner tube 16 generally aligns with or is slightly recessed with respect to the distal end of the central tube 14 when the jaws of the instrument 10 are open, thereby positioning the proximal end of the inner tube 16 within the handle member 1. The inner tube 16 has a lumen 24 that extends the entire length thereof. A conductive lead 18 extends the entire length of the inner tube 16 through the lumen 24. The distal end of the lead 18 is preferably configured to provide three shaped zones 26, 28, 30. The first zone 26 is angled upwardly from the immediately proximal longitudinal axis of the lead 18 to thereby form an upward ramp 32. The second zone 28 is angled downwardly, while the third zone 30 is angled forwardly to be substantially parallel with the axis of the lead 18 immediately proximal to the ramp 32 to thereby function as an opposing second electrode jaw 36. While the second zone 28 is shown in the drawing figures as a relatively sharp angle from the first zone 26, it is to be understood that the term "angled downwardly" in reference to the second zone 28 includes a more gradual angle or other downward-slope as would be apparent to a skilled artisan to thereby still attain meetability of the jaws 34, 36. A conductive metal sleeve 37 can be secured to the third zone 30 and be flattened thereabout to increase the size of the second jaw 36 to be comparable to that of the first jaw 34. The proximal end of the lead 18 terminates in a free wheeling electrical connector 4 which cannot move translationally in the handle member 1, but can freely rotate. The electrode jaws 34, 36 can be serrated on their mating surfaces to form a gripping surface. The jaws 34, 36 are not insulated from one another, except by the air gap existing when the jaws are apart. Contact of the jaws 34, 36 is accomplished by moving the inner tube 16 in the distal direction inside the lumen of the central tube 14. A slot 15 (FIG. 5) is disposed in the top distal portion of the central tube 14 and is of sufficient longitudinal length to accommodate the first zone 26 of the lead 18. At least the portion of the lead 18 which thereby comes in contact with the central tube 14 in the vicinity of the slot 15 is insulated as with polyamide so that electrical shorting cannot occur. Provision of the slot 15 keeps the circumferential remainder of the central tube 14 thereat surrounding the inner tube 16 to thereby prohibit the inner tube 16 from merely riding over the first zone 26 of the lead 18 without forcing it toward the central tube 14. Because the lead 18 is fastened to the free wheeling connector 4, which cannot move translationally, the inner tube 16 can slide over the stationary conductive lead 18 to thereby close the jaws 34, 36 as a proximal portion of the ramp 32 enters the inner tube 16 to thereby move the second jaw 36 toward the first jaw 34. RF energy is delivered to the central tube 14 by a wire conductor 17 passing through the spool 45 to the tube 14 and connecting proximally to the connector 4.

The inner tube 16 is made to move translationally inside the central tube 14 and over the lead 18 by effecting longitudinal displacement of a slidable spool mechanism 2 located inside the handle 1. When the inner tube 16 is pushed onto the ramp 32 by manipulating the scissors-style handle which is operatively coupled to the slidable spool mechanism 2, the distal end of the inner tube 16 forces the second electrode jaw 36 against the first electrode jaw 34. The portion of the lead 18 comprising the ramp 32 may be appropriately insulated so as not to short together when in contact with the outer tube 12 if the outer tube 12 is made of a conductive material. When the inner tube 16 is retracted by the mechanism comprising handle 1 and slidable spool mechanism 2 contained therein, the conductive lead 18 extends sufficiently beyond the distal end of the inner tube 16 to thereby prevent engagement of the ramp 32. Upon such retraction, the jaws 34, 36 will become separated due to the memory property of the conductive lead 18.

With reference to FIGS. 1 and 2, the proximal end of the conductive lead 18 and the central tube 14 are in communication with the free wheeling rotatable electrical connector 4 located in the handle 1. The connector 4 cannot move longitudinally in the handle 1 by virtue of its being contained in a recess formed in the handle. The electrical connector 4 is used to join external leads of an electrosurgical generator (not shown) to the lead 18 and wire conductor 17 leading to the central tube 14. When the electrode jaws 34, 36 are in contact, the generator, activated independently by the user, thereby transmits RF energy through the conductive lead 18 and central tube 14 to the resultant bipolar electrode surfaces of the jaws 34, 36 to cauterize blood vessels or tissue captured therebetween. Cauterization occurs due to the heat transferred to the blood by the RF energy as it propagates between the electrode jaws.

Figure 6:
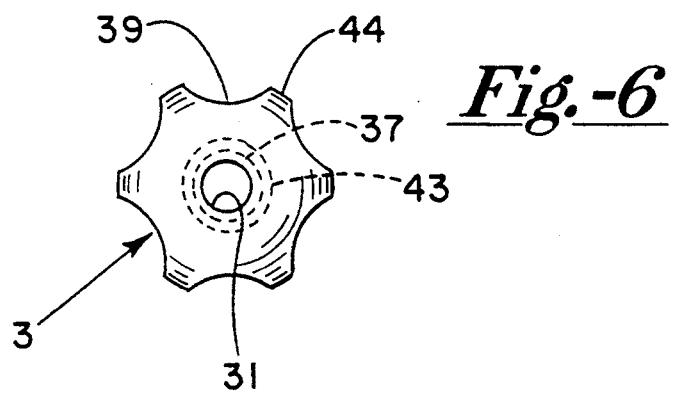
FIG. 6 is a cross-section view of a rotatable knob of the instrument of FIG. 1.

As shown in FIG. 1, the stationary handle is made in two halves 5, each having a longitudinally extending section 6 that terminates at the handle's distal end 7 in a connection 40 with a rotatable knob 3. The proximal end of the handle frame halves 5 terminate in a downward sloping arm 9 that terminates in an annular, finger receiving opening 29. As seen in FIGS. 2 and 6, the rotatable knob 3 is generally cylindrical in shape, having a bore 31 through its center along its central axis. The bore 31 is large enough to accept the outer tube 12 therein and allow the central tube 14 to pass through its lumen. The proximal end 15 of the outer tube 12 is frictionally inserted into the bore 31 of the rotatable knob 3. The front surface 42 of the knob 3 slopes inwardly and rearwardly from the bore 31. The knob 3 has regularly spaced arcuate indentations 39 around its outer diameter 44, allowing a user to readily grip the knob 3 even if it is slippery. The proximal end surface of the rotatable knob 3 abuts the distal end 7 of the handle frame halves 5.

Extending out of the proximal end surface of the knob 3 is an integrally formed tubular extension 41 having a smaller outer diameter 37 (FIG. 6) than the outer diameter 44 of the knob's main body 50. At the end of the extension 41, opposite the knob's main body 50, is an annular flange 52 with a slightly larger diameter 43 than the outer diameter 37 of the extension, but a smaller diameter than the knob's main body diameter 44. As seen in FIG. 1, the knob extension 41 and the flange 52 fit inside the handle frame halves 5 at the handle frame's distal end 7. The handle frame halves 5 are eventually attached together in sandwich fashion to enclose the handle 1 and hold the rotatable knob 3 with extension 41 in place. The knob 3 and the extension 41 are preferably made out of nylon so that the extension 41 can perform as a lubricous bearing for smoother rotation of the knob 3 inside of the handle frame halves 5. The flange 52 of the knob 3 has a hole 56 running perpendicular to the knob's central axis from the outside diameter 43 to the bore 31. The bore 31 passes through the rotatable knob 3, tubular extension 41, and the flange 52.

The proximal end of the inner tube 16 extends completely through the knob bore 31. Extending along the proximal end of the inner tube 16 is a longitudinal groove 54 which runs along the inner tube 16 parallel to its central axis. The groove 54 runs to a spool 45 at the proximal end of the inner tube 16. A screw or pin, inserted into the hole 56 in the flange 52, protrudes into the groove 54 of the inner tube 16 making a spline connection. The pin does not securely fasten the knob 3 to the inner tube 16. Instead, the spline connection allows the inner tube 16 to be translated inside the central tube 14 and knob 3 while still effectively connecting the knob 3 to the inner tube 16. Therefore, when the knob 3 is rotated, the inner tube 16 and electrode jaws 34, 36 will rotate. The spool 45 and inner tube 16 are frictionally fit together. The spool 45 is cylindrical along the central axis of the inner tube 16 and has two end flanges 58, one at each end. The spool 45 is part of the slidable spool mechanism 2 used for a reciprocally moving the inner tube 16 longitudinally within the translationally stationary outer tube 12, central tube 14 and knob 3. The other part of the slidable spool mechanism 2 is a pivotally mounted lever arm 60 secured by a pivot pin to the stationary handle frame halves 5 on the section 6 just below a slot 73 formed in the frame 5. The slot 73 is large enough to accommodate the spool 45 and a bifurcated end 51 of the pivotally mounted arm 60. The bifurcated end 51 engages opposing side surfaces of the spool 45 between the spool's two flanges 58. The coupling allows the spool 45, inner tube 16, central tube 14, outer tube 12 and conductive lead 18 to rotate. The bifurcated end 51 contacts the flanges 58 of the spool 45 when the arm 60 is manipulated, thus, moving the spool 45 and inner tube 16 back and forth longitudinally.

As shown, the bottom grip on arm 60 comprises an opening 64 for a finger and a downward protruding hook 55 for another finger. The hook 55 curves towards the distal end 7 of the handle frame 5 when the movable arm element 60 is pivotally mounted to the stationary frame element 5 at pin location 75. By pulling the bottom grip 53 toward the stationary handle 9, the bifurcated end 51 of the pivotally mounted movable arm element 60 moves toward the distal end 7 of the handle frame 5 and thereby urges the spool 45 toward the distal end 7 of the handle 1. Movement of the spool 45 and therefore the inner tube 16, which is frictionally fit in the spool 45, moves the distal end of the inner tube 16 over a portion of the ramp 32, thus causing the second electrode jaw 36 to contact the first electrode jaw 34. By pushing the bottom grip 53 of the pivotally mounted arm 60 toward the distal end 57 of the handle frame 5, the bifurcated end 51 of the pivotally mounted arm 60 moves toward the proximal end 8 of the handle 1. This pulls the spool 45 and the inner tube 16 toward the proximal end 8 of the handle 1. The portion of the ramp 32 formerly within the distal end of the inner tube 16 is thereby released and the electrode jaws 34, 36 open. The scissor action just described is the preferred means for achieving translational motion of the inner tube 16 within the translationally stationary central tube 14 and over the conductive lead 18.

A finger activated safety catch or trigger 70 is provided to stop movement of the bifurcated end 51 of the arm 60 in the direction of the distal end 7 of the handle frame 5. The trigger 70 introduces a preset gap to prevent complete closure of the jaws 34, 36. The trigger 70, preferably made out of a medical grade plastic, such as a 20% glass filled polycarbonate material, is crescent-moon shaped with the concave side facing toward the distal end 7 of the handle frame 5 and the convex side facing toward the proximal end 7 of the handle 1. The trigger 70 has a bifurcated top with one prong of the top 74 pivotally attached to the distal end 7 of the handle frame 5 and the other prong 76 really swinging toward the proximal end 8. The freely swinging prong 76 will loosely slide between the handle frame 5 and the bifurcated end 51 of the arm 60 when the trigger 70 is pulled toward the proximal end 8 of the handle member 1. The freely swinging prong 76 when situated between the handle frame 5 and bifurcated end 51 stops movement toward the distal end 7 of the bifurcated end 51 and stops further translational movement of the spool 45 and inner tube 16 in the direction of the distal end of the central tube 14. This stops the inner tube 16 from sliding over the ramp 32 and thereby prevents the electrode jaws 34, 36 from closing completely. To allow more complete closure of the jaws 34, 36, the trigger 70 is pushed toward the distal end 7 of the handle frame 5 removing the freely swinging prong 76 from its location between the handle frame 5 and the bifurcated end 51 of the pivotally mounted arm 60. The pivotally mounted arm 60 is then free to be pulled closer to the proximal end 8 of the handle member 1. This forces the distal end of the inner tube 16 to slide further over the ramp 32 and close the jaws 34, 36 more completely.

Finally, to hold all parts of the handle member ! together, the two handle halves 5 are securely fastened together. The fit is accomplished by lining up opposing pin and hole arrangements 57 in opposing pieces 5 and ultrasonically or otherwise bonding the handle halves together along their peripheral edges.

In use, a physician or other operator inserts as much of the length 22 of the instrument 10 into an endoscope, laparoscope or similar device as required to position the distal end of the instrument 10 at the site of treatment. As coagulation activity is required, the operator maneuvers the open jaws 34, 36 to position the tissue or vessel to be affected therebetween, and thereafter, with RF energy applied, manipulates the arm 60 of the handle member 1 to close the gap between the jaws 34, 36 and simultaneously effectuate coagulation.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

I claim:
1. A bipolar coagulation instrument comprising:
 (a) a first, elongated, non-conductive, outer tube having a proximal end and a distal end;
 (b) a second, elongated, electrically conductive, central tube coaxially disposed within the outer tube and extending distally beyond said distal end of said outer tube, said central tube having a proximal end adapted for communication with an energy source and a distal end portion, with said distal end portion comprising a floor portion only which functions as a first jaw of the instrument;
 (c) a third, elongated, non-conductive, inner tube coaxially disposed within the central tube and translationally movable within said central tube;
 (d) an electrically conductive lead member coaxially disposed within the inner tube and extending distally therefrom the same distance as said central tube extends distally from said distal end of said outer tube, said lead member having a proximal end adapted for communication with an energy source and a distal end portion, with said distal end portion configured into a first shaped zone angled upwardly from an immediately proximal longitudinal axis of the lead member to thereby form an upward ramp, a second shaped zone angled downwardly from the first shaped zone, and a third shaped zone angled forwardly from the second shaped zone to be substantially parallel with the longitudinal axis of the lead member immediately proximal to the first shaped zone to thereby function as an opposing second jaw to the first jaw; and
 (e) a handle member comprising means for translationally moving the inner tube to thereby force the second jaw against the first jaw and thereafter release the second jaw from the first jaw.

2. A bipolar coagulation instrument as claimed in claim 1 wherein the handle member comprises a stationary element coupled to the proximal end of the outer tube and a movable element pivotably joined to said stationary element with said moveable element having a first end coupled to a proximal end of the inner tube, and a second end of said moveable element configured for manual manipulation.

3. A bipolar coagulation instrument as claimed in claim 1 and further including selectively actuatable means for limiting the extent of said translational movement of said inner tube.

4. A bipolar coagulation instrument as in claim 2 wherein said stationary element and said movable element include a scissors-style grip.

5. A bipolar coagulation instrument as in claim 2 and further including a trigger member operatively coupled between said stationary element and said movable element for selectively limiting the extent or movement of said movable element.

6. A bipolar coagulation instrument as claimed in claim 4 wherein said handle member further includes a spool member affixed to the proximal end of said inner tube and said moveable element includes a bifurcated end engaging said spool member.

7. A bipolar coagulation instrument as in claim 4 wherein said handle member further includes a knob journaled for rotation on said stationary member, said knob including means for coupling it to said inner tube whereby rotation of said knob imparts rotation to said inner tube and manual manipulation of said scissors-style grip imparts longitudinal displacement of said inner tube.

* * * * *

UNITED STATES PATENT AND TRADEMARK OFFICE
CERTIFICATE OF CORRECTION

PATENT NO. : 5,342,359
DATED : August 30, 1994
INVENTOR(S) : Mark A. Rydell

It is certified that error appears in the above-indentified patent and that said Letters Patent is hereby corrected as shown below:

Column 8, line 26, delete "and" and put instead -- end --.

Signed and Sealed this

Twenty-second Day of November, 1994

Attest:

BRUCE LEHMAN

*Attesting Officer*  *Commissioner of Patents and Trademarks*